(12) United States Patent
Caetano et al.

(10) Patent No.: US 9,241,893 B2
(45) Date of Patent: Jan. 26, 2016

(54) TOPICAL COSMETIC SKIN LIGHTENING COMPOSITIONS AND METHODS OF USE THEREOF

(75) Inventors: Joao Paulo Caetano, Sao Paulo (BR); Monica Alves Mariani De Oliveira, São Pauloa (BR)

(73) Assignee: Stiefel Laboratories, Inc., Wilmington, New Castle, DE (US)

( * ) Notice: Subject to any disclaimer, the term of this patent is extended or adjusted under 35 U.S.C. 154(b) by 640 days.

(21) Appl. No.: 12/743,353

(22) PCT Filed: Nov. 19, 2008

(86) PCT No.: PCT/US2008/012952
§ 371 (c)(1),
(2), (4) Date: Apr. 12, 2011

(87) PCT Pub. No.: WO2010/059140
PCT Pub. Date: May 27, 2010

(65) Prior Publication Data
US 2011/0182835 A1 Jul. 28, 2011

Related U.S. Application Data

(63) Continuation-in-part of application No. PCT/US2007/024109, filed on Nov. 19, 2007.

(51) Int. Cl.
| | | |
|---|---|---|
| *A61K 8/97* | (2006.01) | |
| *A61K 36/28* | (2006.01) | |
| *A61K 36/47* | (2006.01) | |
| *A61K 36/484* | (2006.01) | |
| *A61Q 19/02* | (2006.01) | |

(52) U.S. Cl.
CPC . *A61K 8/97* (2013.01); *A61K 36/28* (2013.01); *A61K 36/47* (2013.01); *A61K 36/484* (2013.01); *A61Q 19/02* (2013.01); *A61K 2800/592* (2013.01)

(58) Field of Classification Search
CPC ......... A61K 8/97; A61K 36/28; A61K 36/47; A61K 36/484; A61K 2800/592; A61K 2300/00; A61Q 19/02
See application file for complete search history.

(56) References Cited

U.S. PATENT DOCUMENTS

| | | | |
|---|---|---|---|
| 5,609,875 A | 3/1997 | Hadas | |
| 6,090,369 A * | 7/2000 | Stewart | 424/59 |
| 2001/0016213 A1 | 8/2001 | Singh-Verma | |
| 2003/0198612 A1 | 10/2003 | Chaudhuri et al. | |
| 2004/0028642 A1 | 2/2004 | Hansenne et al. | |
| 2004/0175439 A1 | 9/2004 | Cyr | |
| 2006/0018867 A1 | 1/2006 | Kawasaki et al. | |
| 2006/0280704 A1 | 12/2006 | John | |
| 2007/0020203 A1 * | 1/2007 | Chaudhuri et al. | 424/59 |
| 2007/0122492 A1 | 5/2007 | Behr | |
| 2008/0050459 A1* | 2/2008 | Elie et al. | 424/757 |

FOREIGN PATENT DOCUMENTS

| | | | | |
|---|---|---|---|---|
| DE | WO2005/063191 | * | 7/2005 | A61K 7/48 |
| JP | 01-311011 A | | 12/1989 | |
| JP | 06-271442 A | | 9/1994 | |
| JP | 09-077638 A | | 3/1997 | |
| JP | 2003-063925 A | | 3/2003 | |
| JP | 2003-081749 A | | 3/2003 | |
| JP | 2004-352697 A | | 12/2004 | |
| JP | 2005-139070 A | | 6/2005 | |
| WO | WO 03/059313 A1 | | 7/2003 | |
| WO | WO 2005/025532 A1 | | 3/2005 | |
| WO | WO 2005/063191 A1 | | 7/2005 | |
| WO | WO 2005/067885 A1 | | 7/2005 | |
| WO | WO2006/053912 | | 5/2006 | |
| WO | WO 2007/107268 A1 | | 9/2007 | |

OTHER PUBLICATIONS

Halder et al., Skin Therapy Letter, vol. 9, issue 6, p. 1 (2004).
Masato Suzuki (Editorial Supervisor), Functional Cosmetics III, CMC Limited, Jan. 1, 2000, pp. 27-35 (in Japanese).
Masato Suzuki (Editorial Supervisor), Functional Cosmetics III, CMC Limited, Jan. 1, 2000 (English translation).

* cited by examiner

*Primary Examiner* — Sean Basquill
(74) *Attorney, Agent, or Firm* — Dara L. Dinner; Theodore R. Furman

(57) ABSTRACT

Topical cosmetic compositions are provided that can comprise a *Phyllanthus* extract, a *Bellis* extract, and a licorice (*Glycyrrhiza*) extract. These compositions are used for topical cosmetic applications, particularly to lighten skin. Methods for lightening skin are also provided and can comprise topically administering a therapeutically effective amount of a topical cosmetic composition comprising a *Phyllanthus* extract, a *Bellis* extract, and a licorice extract, to skin of a subject in need thereof.

24 Claims, 5 Drawing Sheets

Fig. 5 a & b. Photographic Register: Hydroquinone at T0 (day 0) and T21(day 21)

Fig. 5 c & d. Photographic Register: New Formulation at T0 and T21

Fig. 5 e & f. Photographic Register: Control at T0 and T21

TOPICAL COSMETIC SKIN LIGHTENING COMPOSITIONS AND METHODS OF USE THEREOF

This application is a §371 of International Application No. PCT/US2008/012952, filed 19 Nov. 2008, which is a continuation-in-part application of PCT/US2007/024109, filed 19 Nov. 2007.

FIELD OF THE INVENTION

The presently described subject matter relates to topical cosmetic or dermatological compositions comprising plant extracts. These compositions are used for topical cosmetic applications, particularly to treat undesired skin pigmentation.

BACKGROUND OF THE INVENTION

Topical cosmetic skin lightening compositions that are safe and effective are particularly desirable for treating undesirable skin pigmentation, including for example, regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, known as liver spots; accidental hyperpigmentation such as post-lesional photosensitization and scarring; skin ageing (for example lentigines seniles); and certain forms of leukoderma such as vitiligo where, if the injured skin cannot be repigmented, the residual zones of normal skin are lightened or depigmented to impart a homogeneous color to the entire skin.

Several active ingredients and preparations that lighten skin, i.e., counteract skin pigmentation, are currently known. These products that are currently used contain hydroquinone, but such products have recently been deemed unacceptable for toxicological reasons. In fact, RDC 215 forbids the use of hydroquinone in cosmetic products after December, 2007.

U.S. Published Patent Application No. 2008/0050459 describes a cosmetic composition comprising an extract of *Phyllanthus Embilica*, an extract of *Bellis Perrenis*, an extract of *Glycyrrhiza Glabra*, and requiring at least one oligopeptide to achieve its cosmetic effect for the combined cosmetic treatment of fine lines and wrinkles, and/or skin brightening. Suitable oligopeptides are described as those having a suitable molecular weight so that they are able to act as carriers of *Phyllanthus Embilica* extract and penetrate skin to maximize the efficacy. The only oligopeptides described in the publication for achieving the cosmetic composition are oligopeptide-4 (pro-collagen oligopeptide) and oligopeptide-5 (pro-elastin oligopeptide).

There remains a need in the art for improved topical cosmetic compositions containing agents that safely and effectively lighten skin.

SUMMARY OF THE INVENTION

The present subject matter relates generally to topical cosmetic compositions useful for treating various skin disorders or conditions associated with undesired skin pigmentation. Further, the present subject matter relates to topical cosmetic compositions useful for cosmetic lightening of skin areas whose pigmentation is adequate for the individual skin type.

In an embodiment, the present subject matter relates to a topical cosmetic composition, comprising, consisting essentially of, or consisting of a *Phyllanthus* extract; a *Bellis* extract; and a licorice extract. In one embodiment, the cosmetic composition does not comprise at least one oligopeptide. In another embodiment, the cosmetic composition does not comprise at least one oligopeptide that is not normally present in *Phyllanthus* extract, *Bellis* extract, or licorice extract. In a further embodiment, the cosmetic composition does not comprise oligopeptide-4 (pro-collagen oligopeptide) or oligopeptide-5 (pro-elastin oligopeptide). In another embodiment, the cosmetic composition does not comprise at least one oligopeptide having a suitable molecular weight so that it is able to act as carrier of *Phyllanthus Embilica* extract and penetrate skin to maximize the efficacy.

In an embodiment, the present subject matter relates to a topical cosmetic composition, comprising, consisting essentially of, or consisting of a *Phyllanthus embilica* extract; a *Bellis perennis* extract; and a licorice extract.

In another embodiment, the present subject matter relates to a topical cosmetic composition, comprising, consisting essentially of, or consisting of a skin-lightening active component comprising, consisting essentially of, or consisting of a *Phyllanthus* extract, a *Bellis* extract, and a licorice extract; at least one sunscreen; and a cosmetically acceptable carrier.

In another embodiment, the present subject matter relates to a topical cosmetic composition, comprising, consisting essentially of, or consisting of a skin-lightening active component comprising, consisting essentially of, or consisting of a *Phyllanthus embilica* extract, a *Bellis perennis* extract, and a licorice extract; at least one sunscreen; and a cosmetically acceptable carrier.

In an embodiment, the present subject matter relates to a topical cosmetic composition, comprising, consisting essentially of, or consisting of a skin-lightening active component comprising, consisting essentially of, or consisting of a *Phyllanthus* extract, a *Bellis* extract, and a licorice extract; and a non-skin lightening component comprising at least one sunscreen.

In an embodiment, the present subject matter relates to a topical cosmetic composition, comprising, consisting essentially of, or consisting of a skin-lightening active component comprising, consisting essentially of, or consisting of a *Phyllanthus embilica* extract, a *Bellis perennis* extract, and a licorice extract; and a non-skin lightening component comprising at least one sunscreen.

In another embodiment, the present subject matter relates to a method of lightening skin pigmentation in a subject, comprising topically administering to skin of a subject in need thereof, a therapeutically effective amount of a topical cosmetic composition in accordance with the presently described subject matter.

In yet another embodiment, the present subject matter relates to a method of treating a skin disorder or condition in a subject, comprising topically administering to skin of a subject in need thereof a therapeutically effective amount of a topical cosmetic composition in accordance with the presently described subject matter.

DETAILED DESCRIPTION

Definitions

Figure 1:
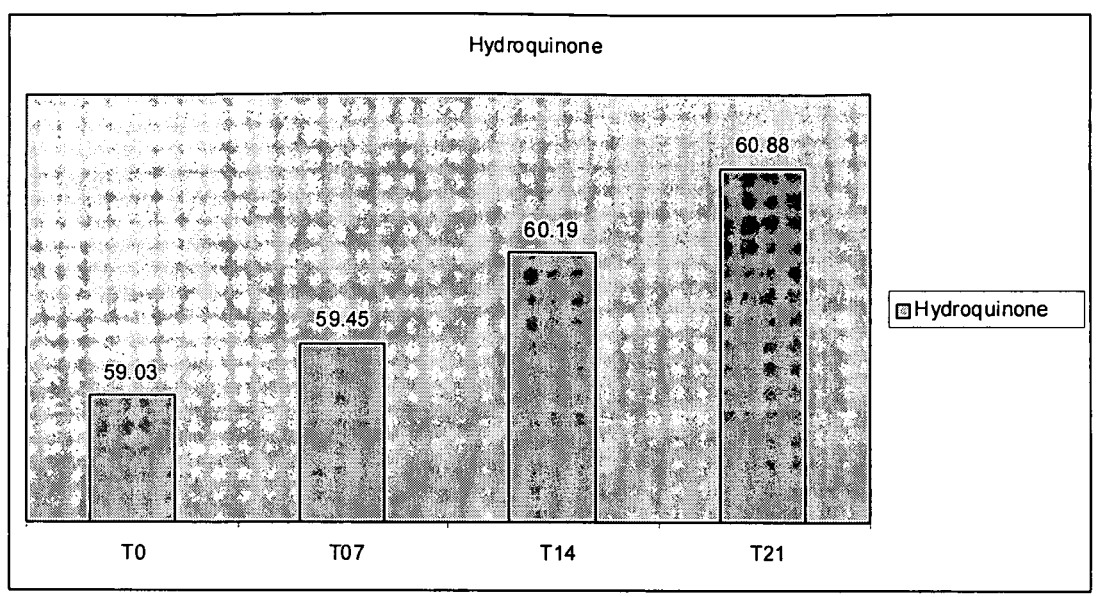
FIG. 1 illustrates progressive lightening over time that becomes statistically significant after 21 days for Site B treated with 2% hydroquinone.

As used herein, the terms "administering", "administration", and like terms refer to any method which, in sound medical or cosmetic practice, delivers the composition to a subject in such a manner as to provide a positive effect on a dermatological disorder, condition, or appearance. The compositions can be administered such that they cover the entire area to be treated.

As used herein "aqueous solvent" refers to a solvent such as water or containing water. Other dissolved components may be present in small amounts, such as, for example, salts, buffers, and other components understood by one of ordinary skill in the art to be optionally present in an aqueous solution.

"Anhydrous formulation" refers to any formulation of the present topical cosmetic composition that does not contain water.

"Cosmetically acceptable" refers to a non-toxic, inert, and/or physiologically compatible composition.

As used herein, the phrases an "effective amount" or a "therapeutically effective amount" of an active agent or ingredient, which are synonymous herein, refer to an amount of the active agent sufficient enough to have a positive effect on the area of application. Accordingly, these amounts are sufficient to modify the skin disorder, condition, or appearance to be treated but low enough to avoid serious side effects, within the scope of sound medical or dermatological advice.

As used herein, "extract" refers to one or more components isolated from a plant source in a fluid or powder form. The plant source can comprise or consist of the entire plant or one or more parts of the plant, for example, the plant fruit, flower, root, leaves, stems, and/or bark. A fluid or liquid extract can be dried, for example, spray dried or desiccated, to form a powder. The extract can be a mixture of one or more components from a plant in a fluid and/or powder form.

By "non-skin lightening" is meant any compound, substance or composition; or agent; or component comprising, consisting essentially of, or consisting of one or more agents, substances, compounds and compositions, which upon topical application to skin does not depigment or lighten the skin. Such agents can include, for example, one or more active agents, for example, a sunscreen, an anti-acne agent, an anti-microbial agent, an anti-wrinkle agent, an anti-atrophy agent, an anti-inflammatory agent, and an optical brightener; and/or one or more cosmetically acceptable excipients, for example, a thickener, a chelating agent, a moisturizer, an emollient, a humectant, a gelling agent, a pH adjuster, a surfactant, a stabilizer, a vitamin, a penetration enhancer, a perfume, a coloring agent, and a solvent; and/or combinations thereof; as described herein.

As used herein, "pharmaceutically acceptable free bases, salts, esters, or solvates" refers to free bases, salts, esters, or solvates of subject compound(s) which possesses the same pharmacological activity as the subject compound(s) and which are neither biologically nor otherwise undesirable. A salt, ester, or solvate can be formed with, for example, organic or inorganic acids. Water or oil-soluble or dispersible products are thereby obtained.

As used herein, "oligopeptide" refers to a peptide having a suitable molecular weight so that it is able to act as a carrier of *Phyllanthus Embilica* extract and penetrate skin. Oligopeptides that might act as carriers of *Phyllanthus Embilica* extract and penetrate skin include oligopeptide-4 (pro-collagen oligopeptide) and oligopeptide-5 (pro-elastin oligopeptide). As used herein, "oligopeptide" does not refer to any peptide that is normally present in *Phyllanthus* extract, *Bellis* extract, or licorice extract. It is noted that in an embodiment of the present subject matter, the cosmetic composition does not comprise at least one oligopeptide that is not normally present in *Phyllanthus* extract, *Bellis* extract, or licorice extract.

As used herein, "serum" refers to a hydrophilic liquid formulation. A serum may optionally be free from one or more of an emollient, a wax and a silicone.

As used herein, "skin lightening agent" refers to any compound, substance, or composition which upon topical application to skin lightens or depigments the skin. Such skin lightening agents can include, but are not limited to, pigmentation inhibitors, tyrosinase inhibitors, and melanocyte melanogenesis inhibitors.

As used herein, "synergistic skin lightening system" or "synergistic skin lightening component" refers to a skin lightening active component comprising, consisting essentially of, or consisting of a *Phyllanthus embilica* extract, a *Bellis perennis* extract, and a licorice extract, that exhibits synergistic skin lightening efficacy as compared to the skin lightening efficacy of each individual skin lightening active agent. In this regard, the combination of these ingredients provides a greater than additive skin lightening effect.

As used herein, a "treatment" or "treating" of a skin disease, disorder, or condition encompasses alleviation of at least one symptom thereof, a reduction in the severity thereof, or the delay, prevention, or inhibition of the progression thereof. Treatment need not mean that the disease, disorder, or condition is totally cured. A useful composition herein needs only to reduce the severity of a skin disease, disorder, or condition, reduce the severity of symptoms associated therewith, provide improvement to a patient's quality of life, or delay, prevent, or inhibit the onset of a skin disease, disorder, or condition.

It is noted that, as used in this specification and the appended claims, the singular forms "a," "an" and "the" include plural references unless the context clearly dictates otherwise.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Topical Cosmetic Compositions

The present subject matter relates to a topical cosmetic composition, comprising, consisting essentially of, or consisting of a *Phyllanthus* extract; a *Bellis* extract; and a licorice extract.

Primary Skin Lightening Active Agents

In accordance with the presently described subject matter, the present topical cosmetic compositions can comprise or consist of a *Phyllanthus* extract, i.e., *Phyllanthus embilica* extract; a *Bellis* extract, i.e., a *Bellis perennis* extract; and a licorice extract.

"*Phyllanthus* extract" means an extract obtained from the fruit of a member of the *Phyllanthus* genus, including for example, of *Phyllanthus embilica, Phyllanthus niruri* L., *Phyllanthus elegans* Wall, *Phyllanthus iniruri, Phyllanthus reticulatus, Phyllanthus urinaria* L., *Phyllanthus reticulatus* Poir, *Phyllanthus conami* Sw, *Phyllanthus lathyroides* H. B. K., *Phyllanthus casticum* Soy-Will, and *Phyllanthus madagascariensis. Phyllanthus* extract is a safe and effective natural antioxidant.

"*Phyllanthus embilica* extract" means a standardized extract of *Phyllanthus embilica*, including for example, EMBLICA® (Merck KGaA, Darmstadt, Germany and EM industries, Inc., USA, an affiliate of Merck KGaA). *Phyllanthus embilica* is also commonly known as "*Emblica officinalis* Gaertn" and is a member of the family "Euphorbiaceae." *Phyllanthus embilica* is a very rich source of vitamin C, having an ascorbic acid content in the range from 1000 to 1800 mg per 100 grams of fruit. *Phyllanthus embilica* extract is a safe and effective natural antioxidant that has no pro-oxidation activity and can exhibit dual functionality, i.e., chelation and antioxidant. Unlike most antioxidants that go from an active to an inactive form, *Phyllanthus embilica* extract can exhibit a cascading effect that provides long-lasting and stable antioxidant activity. *Phyllanthus embilica* extract can be produced by extracting premium quality fruits using a water-based process as described in U.S. Pat. No. 6,124,268, incorporated herein by reference in its entirety. *Phyllanthus embilica* extract typically contains low-molecular weight tannins, namely Emblicanin A and Emblicanin B, along with Pedunculagin and Punigluconin, Rutin and Gallo-ellagitannoids.

"*Bellis* extract" means an extract obtained from a member of the *Bellis* genus, including for example, the extract obtained from the flowers of a member of the *Bellis* genus, for example, from *Bellis perennis* flowers and/or from *Bellis rotundifolia* L. flowers. The *Bellis* extract can comprise or consist of one or more bioactive molecules including saponins (triterpene glycosides), polyphenols (phenolic acid), flavonoid glycosides, polysaccharides and inulin.

"*Bellis perennis* extract" means the extract obtained from *Bellis perennis* flowers that can comprise or consist of one or more bioactive molecules including saponins (triterpene glycosides), polyphenols (phenolic acid), flavonoid glycosides, polysaccharides and inulin.

Suitable *Bellis perennis* extracts can include BELIDES® available from CLR Chemisches Laboratorium, Berlin, Germany. *Bellis perennis* is also commonly known as *Bellis alpina* Hegetschw., *Bellis hortensis* Mill., *Bellis hybrida* Ten., *Bellis integrifolia* DC., and *Bellis scaposa* Gilib.

"Licorice extract" means an extract obtained from a member of the *Glycyrrhiza* genus, for example obtained from the root of a member of the *Glycyrrhiza* genus. The genus "*Glycyrrhiza*" is a member of the family "Fabaceae." Suitable *Glycyrrhiza* extracts can include the oil soluble licorice extract available from Bioland, Korea. Other suitable *Glycyrrhiza* extracts can be obtained from one or more of the following members of the *Glycyrrhiza* genus including *Glycyrrhiza echinata* L. (Chinese licorice), *Glycyrrhiza glabra* L. (cultivated licorice), *Glycyrrhiza lepidota* L., *Glycyrrhiza glutinosa*, polypodium *Glycyrrhiza, Glycyrrhiza brachycarpa* Boiss., *Glycyrrhiza germanica* Tourn., *Glycyrrhiza glandulifera* Waldst. et Kit., Glycyrrhiza hirsuta L., *Glycyrrhiza laevis* Pall., *Glycyrrhiza officinalis* Lepech., *Glycyrrhiza pallida* Boiss., *Glycyrrhiza siliquosa* Tourn., *Glycyrrhiza violacea* Boiss., *Glycyrrhiza viscosa* Turcz. ex Ledeb., *Glycyrrhiza vulgaris* Gueldenst. ex Ledeb, *Liquiritia officinalis* Moench, and *Liquiritia officinarum* Medik.

In an embodiment, the present topical cosmetic composition can comprise or consist of a skin lightening active component that can comprise or consist of a *Phyllanthus* extract, a *Bellis* extract, and a licorice extract.

In an embodiment, the present topical cosmetic composition can comprise or consist of a skin lightening active component that can comprise or consist of a *Phyllanthus embilica* extract, a *Bellis perennis* extract, and a licorice extract.

In an embodiment, the present subject matter relates to a topical cosmetic composition wherein the total skin lightening active component is present in the topical cosmetic composition in an amount of from about 0.5% to about 43% by weight, from about 1% to about 30% by weight, from about 1.5% to about 23% by weight, from about 1.5% to about 15% by weight, from about 3% to about 10% by weight, from about 6% to about 8% by weight, or about 7.05% by weight, based on the total weight of the composition.

In another embodiment, the present subject matter relates to a topical cosmetic composition wherein the *Phyllanthus* extract, for example, the *Phyllanthus embilica* extract, is present in the topical cosmetic composition in an amount of from about 0.1% to about 8% by weight, from about 0.25% to about 4% by weight, from about 0.5% to about 3% by weight, from about 0.5% to about 2% by weight, from about 1% to about 2% by weight, or about 2% by weight, based on the total weight of the composition.

In a further embodiment, the present subject matter relates to a topical cosmetic composition wherein the *Bellis* extract, for example, the *Bellis perennis* extract, is present in the topical cosmetic composition in an amount of from about 0.5% to about 30% by weight, from about 1% to about 20% by weight, from about 2% to about 10% by weight, from about 3% to about 7% by weight, from about 4% to about 6% by weight, or about 5.0% by weight, based on the total weight of the composition.

In yet another embodiment, the present subject matter relates to a topical cosmetic composition wherein the licorice extract is present in the topical cosmetic composition in an amount of from about 0.005% to about 5% by weight, from about 0.01% to about 2% by weight, from about 0.01% to about 1% by weight, from about 0.02% to about 0.08% by weight, from about 0.03% to about 0.07% by weight, or about 0.05% by weight, based on the total weight of the composition.

In another embodiment, the present subject matter relates to a topical cosmetic composition wherein the *Phyllanthus* extract, for example, the *Phyllanthus embilica* extract, is present in the topical cosmetic composition in an amount of from about 0.50 wt % to about 2 wt %; the *Bellis* extract, for example, the *Bellis perennis* extract, is present in the topical cosmetic composition in an amount of from about 1 wt % to about 20 wt %; and the licorice extract is present in the topical cosmetic composition in an amount of from about 0.01 wt % to about 1 wt %.

In yet another embodiment, the present subject matter relates to a topical cosmetic composition, wherein the *Phyllanthus embilica* extract is present in the topical cosmetic composition in an amount of about 2 wt %; the *Bellis perennis* extract is present in an amount of about 5 wt %; and the licorice extract is present in the topical cosmetic composition in an amount of about 0.05 wt %.

In an embodiment, the present subject matter relates to a topical cosmetic composition, comprising, consisting essentially of, or consisting of a skin-lightening active component comprising, consisting essentially of, or consisting of a *Phyllanthus* extract, for example, a *Phyllanthus embilica* extract; a *Bellis* extract, for example, a *Bellis perennis* extract; and a licorice extract; at least one sunscreen; and a cosmetically acceptable carrier. The cosmetically acceptable carrier can comprise or consist of one or more cosmetically acceptable excipients.

In another embodiment, the present subject matter relates to a topical cosmetic composition, comprising, consisting essentially of, or consisting of a skin-lightening active component comprising, consisting essentially of, or consisting of a *Phyllanthus* extract, for example, a *Phyllanthus embilica* extract; a *Bellis* extract, for example, a *Bellis perennis* extract; and a licorice extract; and a non-skin lightening component. The non-skin lightening component can comprise or consist of one or more of an active agent, for example, a sunscreen; a cosmetically acceptable carrier; and/or a cosmetically acceptable excipient, as described herein.

In a further embodiment, the present subject matter relates to a topical cosmetic composition in accordance with the subject matter described herein that can comprise one or more non-skin lightening active agents.

In yet another embodiment, the topical cosmetic composition and/or the cosmetically acceptable carrier and/or one or more cosmetically acceptable excipients, can be free from any skin lightening agents other than a *Phyllanthus* extract, for example a *Phyllanthus embilica* extract; a *Bellis* extract, for example, a *Bellis perennis* extract; and licorice extract. The topical cosmetic composition and/or the cosmetically acceptable carrier and/or one or more cosmetically acceptable excipients, can be free from any plant derived skin lightening agents other than a *Phyllanthus* extract, for example a *Phyllanthus embilica* extract; a *Bellis* extract, for example, a *Bellis perennis* extract; and licorice extract. The topical cosmetic composition and/or the cosmetically acceptable carrier and/or one or more cosmetically acceptable excipients can be free from any non-plant derived skin lightening agents.

In an embodiment, the present subject matter relates to a topical cosmetic composition, wherein the composition and/or a skin lightening active component and/or a non-skin lightening component, does not comprise hydroquinone or a derivative thereof, and/or does not comprise a polyorganosiloxane-containing epsilon-polylysine compound, and/or does not comprise a flavan.

Synergistic Skin Lightening Component

In another embodiment, the present subject matter relates to a topical cosmetic composition that can comprise or consist of a synergistic skin lightening active component comprising, consisting essentially of, or consisting of a *Phyllanthus* extract, for example a *Phyllanthus embilica* extract; a *Bellis* extract, for example, a *Bellis perennis* extract; and licorice extract, wherein the synergistic skin lightening active component exhibits synergistic skin lightening efficacy as compared to the skin lightening efficacy of each individual skin lightening active agent.

In an embodiment, the present subject matter relates to a synergistic skin lightening component for use in a topical cosmetic composition comprising, consisting essentially of, or consisting of a *Phyllanthus* extract, for example a *Phyllanthus embilica* extract; a *Bellis* extract, for example, a *Bellis perennis* extract; and licorice extract.

In another embodiment, the present subject matter relates to a synergistic skin lightening component for use in a topical cosmetic composition comprising, consisting essentially of, or consisting of a *Phyllanthus* extract, for example a *Phyllanthus embilica* extract; a *Bellis* extract, for example, a *Bellis perennis* extract; and licorice extract, wherein the synergistic skin lightening component demonstrates enhanced skin lightening efficacy. The synergistic skin lightening component can be free from hydroquinone.

In an embodiment, the topical cosmetic composition in accordance with the presently described subject matter, can comprise or consist of a skin lightening active component that exhibit's synergistic skin lightening efficacy.

In a further embodiment, the topical cosmetic composition in accordance with the presently described subject matter, can comprise or consist of a skin lightening active component that exhibits synergistic skin lightening efficacy, wherein the topical cosmetic composition is free from hydroquinone.

In an embodiment, the topical cosmetic composition or the synergistic skin lightening system, in accordance with the presently described subject matter, can comprise or consist of a skin lightening active component that exhibits synergistic skin lightening efficacy, wherein the topical cosmetic composition is free from hydroquinone and/or a flavan and/or a polyorganosiloxane-containing epsilon-polylysine compound.

Cosmetically Acceptable Carrier

Any non-toxic, inert, and effective topical cosmetically acceptable carrier may be used to formulate the compositions described herein. Well-known carriers used to formulate other topical therapeutic compositions for administration to humans are useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful cosmetically acceptable excipients, carriers and diluents include distilled water, physiological saline, Ringer's solution, dextrose solution, Hank's solution, and DMSO, which are among those suitable for use herein.

These additional other inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 17th Ed., Mack Publishing Co., Easton, Pa. (1990), both of which are incorporated by reference herein in their entirety.

Sunscreens

In another embodiment, the present subject matter relates to a topical cosmetic composition that can comprise at least one sunscreen. The at least one sunscreen can be present in an amount of from about 0.5% to about 30% by weight based on the total weight of the topical cosmetic composition, from about 1% by weight to about 20% by weight, or from about 1% by weight to about 10% by weight based on the total weight of the composition.

Suitable sunscreens can include broad-spectrum sunscreens that protect against both UVA and UVB radiation, or sunscreen agents that protect against UVA or UVB radiation.

In an embodiment, the present topical cosmetic compositions can comprise a sunscreen comprising or consisting of one or more of methylene bis-benzotriazolyl tetramethylphenol, diethylamino hydroxybenzoyl hexyl benzoate, coated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

In an additional embodiment, the present topical cosmetic compositions can comprise a sunscreen comprising one or more of methylene bis-benzotriazolyl tetramethylphenol (TINOSORB M available from CIBA), diethylamino hydroxybenzoyl hexyl benzoate, and coated zinc oxide, in an amount of from about 1% to about 20% by weight, from about 2% to about 10% by weight, or of about 5% by weight, based on the total weight of the composition. For example, the present topical cosmetic compositions can comprise a sunscreen comprising methylene bis-benzotriazolyl tetramethylphenol in an amount of from about 1% to about 20% by weight, from about 2% to about 10% by weight, or of about 5% by weight, based on the total weight of the composition In a further embodiment, the present topical cosmetic compositions can comprise a sunscreen comprising or consisting of one or more of ethylhexyl methoxycinnamate (available from BASF), isoamyl methoxycinnamate, homosalate ethyl hexyl salicilate, octocrylene, polysilicone-15, butyl methoxydibenzoylmethane, menthyl anthranilate, and ethylhexyl dimethyl PABA, in an amount of from about 1% to about 10%, from about 5% to about 9%, or of about 7.5% by weight, based on the total weight of the composition.

In an embodiment, the present topical cosmetic compositions can comprise one or more sunscreens in an amount of from about 0.5% by weight to about 30% by weight, from about 1% by weight to about 20% by weight, or from about 1% by weight to about 10% by weight based on the total weight of the composition.

In an embodiment, the at least one sunscreen can comprise or consist of a first sunscreen selected from the group consisting of methylene bis-benzotriazolyl tetramethylphenol, diethylamino hydroxybenzoyl hexyl benzoate, and coated zinc oxide; and a second sunscreen selected from the group consisting of ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA. The first sunscreen can be present in an amount of from about 1% to about 20% by weight, and the second sunscreen can be present in an amount of from about 1% to about 10% by weight, based on the total weight of the topical cosmetic composition. The first sunscreen can comprise or consist of methylene bis-benzotriazolyl tetramethylphenol, and the second sunscreen can comprise or consist of ethylhexyl methoxycinnamate.

In an embodiment, the present subject matter relates to a topical cosmetic composition that has an SPF of greater than about 10, has an SPF of greater than about 15, an SPF of at least about 15, an SPF of about 15, an SPF of from about 10 to about 45, an SPF of from about 15 to about 45, or an SPF of from about 15 to about 25.

Aqueous Solvent

The present topical cosmetic compositions can additionally comprise an aqueous solvent. In an embodiment, the present compositions comprise an aqueous solvent, for example, water, in an amount of from about 5% to about 95% by weight, from about 10% to about 90% by weight, from about 25% to about 80% by weight, from about 55% to about 75% by weight, from about 60% to about 70% by weight, or about 63% by weight, based on the total weight of the composition.

Cosmetically Acceptable Excipients

In yet another embodiment, the present subject matter relates to a topical cosmetic composition that can comprise water and at least one cosmetically acceptable excipient. Suitable cosmetically acceptable excipients include those commonly known to one of ordinary skill in the art as useful in topical compositions.

In an embodiment, the at least one cosmetically acceptable excipient can comprise or consist of one or more members selected from the group consisting of an antioxidant, a chelating agent, a pH adjuster, an emollient, a thickening agent, gelling agent, free radical scavenger, a preservative, an emulsifier, a humectant, a moisturizer, a suspending agent, a surfactant, a stabilizer, a vitamin, a penetration enhancer, a perfume or fragrance, a coloring agent, fluid alkyl alcohols, polysiloxanes, modified polysiloxanes, and combinations thereof.

Topical Formulations

In an embodiment, the present topical cosmetic compositions are formulated in a serum, a gel cream, a lotion, a cream, an ointment, a gel, an aerosol, a foam, a foamable liquid, a solution (solubilized system), a paste, a suspension, a dispersion, an emulsion, a skin cleanser, a milk, a mask, a solid stick, a bar (such as a soap bar), an encapsulated formulation, a microencapsulated formulation, microspheres or nanospheres or vesicular dispersions, or other cosmetically acceptable topical dosage form. In the case of vesicular dispersions, the lipids of which the vesicles are made can be of the ionic or nonionic type, or a mixture thereof. The formulation can comprise one or more of an aqueous formulation and/or an anhydrous formulation.

In another embodiment, the present topical cosmetic composition in accordance with the subject matter described herein can comprise or consist of an anhydrous formulation, an aqueous formulation, or an emulsion.

In yet another embodiment, the present topical cosmetic compositions in accordance with the subject matter described herein are formulated in a serum or a gel cream.

Optional Additional Active Agents

The presently described topical cosmetic compositions can optionally further comprise one or more cosmetic active agents or dermatological active agents in addition to the described skin-lightening active agents. Such agents can include, for example, additional skin lightening active agents including plant derived and non-plant derived skin lightening agents, including for example, pigmentation inhibitors, tyrosinase inhibitors, and/or melanocyte melanogenesis inhibitors; and/or non-skin lightening active agents, including for example, optical brightening agents, sunscreen agents, anti-inflammatory agents, anti-microbial agents, anti-fungal agents, anti-wrinkle agents, anti-atrophy agents, anti-acne agents, free-radical scavengers, keratolytic agents, vitamins, anti-elastase and/or anti-collagenase agents, peptides, fatty acid derivatives, steroids, trace elements, extracts of algae and/or of planktons, enzymes and/or coenzymes, flavonoids and/or ceramides, α-hydroxy acids, and combinations thereof.

Methods of Treatment

In an embodiment, the present subject matter relates to a method of lightening skin pigmentation in a subject, comprising topically administering to skin of a subject in need thereof, a therapeutically effective amount of the topical cosmetic composition in accordance with the subject matter described herein.

In another embodiment, the present subject matter relates to a method of treating a skin disorder or condition in a subject, comprising topically administering to skin of a subject in need thereof, a therapeutically effective amount of the topical cosmetic composition in accordance with the subject matter described herein. The skin disorder or condition can be a disorder or condition associated with undesirable skin pigmentation.

In another embodiment, the present subject matter relates to a method of lightening skin pigmentation in a subject or treating a skin disorder or condition in a subject, comprising topically administering for at least once per day for at least three days, for at least five days, for at least seven days, for at least ten days, or for at least fourteen days, to skin of a subject in need thereof, a therapeutically effective amount of the topical cosmetic composition in accordance with the subject matter described herein. In this regard, after three days, five days, seven days, ten days, or fourteen days, respectively, of administration of the present topical compositions the skin is visibly altered.

In an embodiment, the present subject matter relates to a method of lightening skin pigmentation in a subject or treating a skin disorder or condition in a subject, comprising topically administering for at least once per day for at least three weeks to skin of a subject in need thereof, a therapeutically effective amount of the topical cosmetic composition in accordance with the subject matter described herein, wherein after three weeks the skin is visibly lightened.

The present topical cosmetic compositions are effective in treating a variety of skin disorders or conditions characterized by undesirable skin pigmentation. Non-limiting examples of such disorders and/or conditions can include regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, known as liver spots; accidental hyperpigmentation such as post-lesional photosensitization and scarring; freckles; malpigmentation; and certain forms of leukoderma such as vitiligo where, if the injured skin cannot be repigmented, the residual zones of normal skin are lightened or depigmented to impart a homogeneous color to the entire skin. Skin can be treated according to the presently described methods for purely cosmetic lightening of areas, for example, large areas, of skin whose pigmentation, although undesired, is adequate for the individual skin type. In an embodiment, the skin disorder or condition to be treated according to the present methods is undesired skin pigmentation. The administration of the present topical cosmetic composition to areas of the skin that contain undesired pigmentation, lightens those areas.

In a further embodiment, the present subject matter relates to a method of treating a skin disorder or condition in a subject, or to a method of lightening skin pigmentation in a subject, wherein topically administering to skin comprises administering at least once per day or at least twice per day for a period of at least two weeks, at least 3 weeks, or at least 4 weeks, wherein skin pigmentation is lightened.

Methods of Production

Various formulations of the present topical cosmetic compositions in accordance with the presently described subject matter can be readily produced by the skilled artisan according to known methods of producing such formulations including for example, a cream, a gel, a serum, a lotion, or other formulation described herein, without undue experimentation.

A process for producing a cream or emulsion formulation can comprise separately producing an aqueous phase and an oil phase, adding the oil phase to the aqueous phase, for example with mixing and/or homogenization (with high shear), to an emulsion. After the emulsion is produced, one or more of the following components can be optionally added thereto, for example, in the following order, to produce the final emulsion or cream: one or more skin lightening actives; one or more pH adjusters; one or more emollients; one or more skin lightening actives; one or more sunscreen actives; one or more thickening agents; one or more antioxidants; and one or more fragrances. Prior to forming the emulsion, the aqueous phase and the oil phase can be separately heated to a temperature of from about 70° C. to about 99° C.; from about 75° C. to about 95° C.; from about 80° C. to about 90° C.; or about 85° C. After heating the oil phase can be slowly added to the aqueous phase, for example, with mixing and high shear homogenization. The resultant emulsion can then be cooled while maintaining mixing and high shear homogenization, for example, to a temperature of from about 47° C. to about 27° C.; from about 42° C. to about 30° C.; from about 39° C. to about 35° C.; or about 37° C. Thereafter, one or more of the above-described optional components can then be added to the cooled emulsion, for example, with mixing and/or high shear homogenization. The produced emulsion or cream can have a pH of from about 4.5 to 6.5 and/or a viscosity of from about 5,000 cP to about 15,000 cP and/or a density of from about 1.01 to about 1.06.

Further contemplated as within the scope of the present subject matter are topical cosmetic compositions produced according to the above-described processes. If produced according to these processes, these compositions exhibit chemical and physical stability suitable for topical administration.

The topical cosmetic compositions produced according to these processes can be placed in a suitable containment vessel comprising a product contact surface composed of a material selected from the group consisting of glass, plastic, steel, stainless steel, aluminum, Teflon, polymeric structure, ceramic structure, alloys, and mixtures thereof. These containment vessels are used to facilitate manufacturing, handling, processing, packaging, storage, and administration of said topical cosmetic composition. Suitable containment vessels in this regard can be selected from the group consisting of plastic tubes, bottles, metal tubes, and any combination thereof.

Routes of Administration/Dosage

To be effective, the route of administration for topical cosmetic compositions used in the present methods must readily affect the target skin areas. Effective results in most cases are achieved by topical application of a thin layer over the affected area, or the area where one seeks to achieve the desired effect. Effective results can be achieved with application rates from one application every two or three days to four or more applications per day.

Appropriate dosage levels for the active agents contemplated in the present topical cosmetic compositions and methods are well known to those of ordinary skill in the art and are selected to maximize the treatment of the above skin conditions. Dosage levels on the order of about 0.001 mg to about 5,000 mg per kilogram body weight of the skin lightening active components are known to be useful in the treatment of the diseases, disorders, and conditions contemplated herein. Typically, this effective amount of the skin lightening active components will generally comprise from about 0.001 mg to about 100 mg per kilogram of patient body weight per day. Moreover, it will be understood that this dosage of ingredients can be administered in a single or multiple dosage units to provide the desired therapeutic effect.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The present compositions may be given in a single dose or multiple doses daily. In an embodiment, the present topical cosmetic compositions are given from one to four times daily. Starting with a low dose once or twice daily and slowly working up to higher doses if needed is a strategy. The amount of active ingredients that may be combined with the carrier materials to produce a single dosage form will vary depending upon the host treated, the nature of the disease, disorder, or condition, and the nature of the active ingredients. In an embodiment, the topical cosmetic compositions may be topically applied once or multiple times per day. In an embodiment, the present topical cosmetic compositions are topically applied from one to four times daily. For example, starting with once daily and progressing to more frequent applications, if needed, is one strategy.

In an embodiment, the present topical cosmetic compositions are topically applied from one to four times daily, for example, in the morning, at noon, in the afternoon, and/or in the evening.

In an embodiment, the topical cosmetic compositions as described herein can be administered once or multiple times per day for a period of time of at least one week, for a period of at least two weeks, for a period of at least four weeks, or for a period of at least eight weeks. The topical cosmetic compositions can be administered once or multiple times per day for a period of time of up to one year, of up to six months, of up to three months, or of up to two months.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal cosmetic formulations can be determined by one skilled in the art depending upon considerations such as the particular ingredients and the desired dosage. See, for example, *Remington's Pharmaceutical Sciences*, 18th ed. (1990, Mack Publishing Co., Easton, Pa. 18042), pp. 1435-1712, and "Harry's Cosmeticology", 8th ed. (2000, Chemical Publishing Co., Inc., New York, N.Y. 10016), the disclosure of each of which is hereby incorporated by reference herein in its entirety. Such formulations may influence the physical state, stability, rate of in vivo release, and rate of in vivo clearance.

In an embodiment, the present topical cosmetic composition in accordance with the subject matter described herein may be a gel cream packaged in, for example, a tube, or a serum packaged in, for example, a non-aerosol non-foaming pump container or bottle, wherein the amount of the composition contained in the container can be in the range of from about 10 gm to about 60 gm, between about 20 gm and about 50 gm, or about 30 gm, or about 40 gm.

Single dosage kits and packages containing once per day amount of composition may be prepared. Single dose, unit dose, and once-daily disposable containers of the present compositions are contemplated as within the scope of the present subject matter.

The present topical cosmetic compositions in accordance with the subject matter described herein may be formulated for storage in a substantially non-reactive laminated package to enhance stability of the package. This method of storage provides enhanced package stability in comparison with other, paper-based packages.

The amount of composition per single packet may range be from about 0.1 ml to about 20.0 ml, between about 0.5 and about 5.0 ml, or between about 1 and about 3 ml.

In particular, the ability to formulate compositions capable of long term storage, without pre-mixing or compounding requirements prior to application, are also contemplated. Specifically, the present compositions remain unexpectedly stable in storage for periods including between about 3 months and about 3 years, about 3 months and about 2.5 years, between about 3 months and about 2 years, between about 3 months and about 20 months, and alternately any time period between about 6 months and about 18 months.

In an embodiment, the presently described topical cosmetic formulation in accordance with the subject matter described herein remains stable for at least three years at a temperature of less than 30° C. In an embodiment, the presently described topical cosmetic formulation remains stable for at least two years at a temperature of less than or equal to 30° C. In an embodiment, the presently described topical cosmetic formulation remains stable for at least two years at a temperature of less than or equal to 25° C.

EXAMPLES

The following examples are illustrative of the present topical cosmetic compositions and are not intended to be limitations thereon. Any polymer molecular weights are mean average molecular weights. All percentages are based on the percent by weight of the final delivery system or formulation prepared unless otherwise indicated and all totals equal 100% by weight.

Example 1

The following example illustrates the clarifying efficacy of the present topical cosmetic composition as compared to a 2% hydroquinone composition, determined through colorimetry instrumental methodology.

In a monocentric, double-blind, comparative clinical trial over a period of six (6) weeks, the clarifying efficacy of each of two topical products was evaluated in the previously pigmented skin of 10 (ten) volunteers. Dermatological evaluations were performed at the beginning and the end of the study. Skin color was measured by colorimetry, together with the photographic documentation, at T0, T07, T14, and T21. UVB pigmentation was induced in the previously pigmented skin of the volunteers through the use of a light emitting source, i.e., the solar simulator with Xenon arc light 601/300 W, produced by Solar Light CO.

A Minolta Chroma Meter CR400 through a standard color system CIE (The Commission Internacional de l'Eclairage) was used to determine the skin coloration. The color is expressed by a system of three-dimensional coordinates where the L* axis corresponds to skin luminosity, the a* axis corresponds to green and red colors, and the b* axis corresponds to blue and yellow colors.

The solar simulator with Xenon arc light 601/300 W, produced by Solar Light CO, was used as the light source. This equipment provides continuous light emission in the UVB and UVA spectrum, ranging between 290 and 400 nm. The device includes a set of lenses and filters that absorb or disperse irradiation lower than 320 nm or higher than 400 nm. The irradiation occurs through a set of 6 branches of optic fiber called "ports", programmed to apply pre-established individual doses of irradiation. Irradiation monitoring was performed using a Dose Controlling System (DCS), which includes a UVB irradiation detector and an electronic monitor. In this study, only three "ports" were used for each application site of the tested compositions.

Evaluated Samples
1. Hydroquinone 2% (positive control):

| Component | Function | % W/W |
|---|---|---|
| Citric acid | pH adjuster | 0.08 |
| Purified water | vehicle | 67.08 |
| Benzophenone-3 | sunscreen active | 1.5 |
| Octyl methoxycinnamate | sunscreen active | 6 |
| Hydroquinone | lightening agent | 2 |
| Lanette | emulsifier | 13 |
| Sodium metabissulfite | antioxidant | 0.14 |
| Isopropyl palmitate | emollient | 5 |
| Propylene glycol | emollient | 5 |
| Methylparaben | preservative | 0.15 |
| Propylparaben | preservative | 0.05 |
| | | 100.0% |

2. The present topical cosmetic composition comprising:

| Component | Function | % W/W |
|---|---|---|
| Purified water | carrier | 62.250 |
| Cetyl alcohol | thickening agent | 2.2 |
| Butylated hydroxytoluene | antioxidant | 0.050 |
| (C14-22 alcohols and C12-20 alkylglucoside) | emulsifier | 5 |
| Cyclopentasiloxane PEG/PPG-18/18 dimethicone | emollient | 1 |
| Cyclopentasiloxane dimethicone crosspolymer | emollient | 1 |
| Sodium EDTA | chelating agent | 0.2 |
| *Bellis perennis* flower extract | antioxidant/active | 5 |
| *Phyllanthus embilica* fruit extract | antioxidant/active | 2 |
| Licorice extract | antioxidant/active | 0.050 |
| Phenoxyethanol and methylisothiazolinone | preservative | 0.6 |
| Perfume | fragrance | 0.3 |
| Hydroxyethyl acrylate, Sodium acryloyldimethyltaurate copolymer, Squalane, and Polysorbate 60 | thickening agent | 5 |
| Sodium metabisulfite | antioxidant | 0.3 |
| Methylene bis-benzotriazolyl tetramethylphenol | sunscreen active | 5 |
| Ethylhexyl Methoxycinnamate | sunscreen active | 7.5 |
| Propylene glycol | emollient | 2 |
| Triethanolamine | pH adjuster | 0.55 |
| | | 100.0% |

Formulation:
Method of Manufacturing
1. In a suitable vessel disperse the Methylene bis-benzotriazolyl tetramethylphenol in a small quantity of Purified Water. Mix until uniform.
2. In a suitable vessel, blend until uniform the Cyclopentasiloxane PEG/PPG-18/18 dimethicone and Cyclopentasiloxane dimethicone crosspolymer.
3. In a suitable vessel, place the Propylene Glycol. Add and disperse the Licorice Extract. Mix until uniform.
4. In a suitable vessel disperse the Phyllanthus Embilica fruit extract in a small quantity of Purified Water. Mix until uniform.
5. In a suitable vessel disperse the Triethanolamine in a small quantity of Purified Water. Mix until uniform.
6. In a suitable vessel disperse the Sodium Metabisulfite in a small quantity of Purified Water. Mix until uniform.
7. To the main manufacturing vessel, add the remaining Purified Water While mixing, add and disperse the Sodium EDTA. Heat the contents to about 85° C.
8. To a suitable vessel, add the cetyl alcohol, C-14-22 alcohols and C-12-20 alkylglycoside, cetyl alcohol, Ethylhexyl methoxycinnamate, and Butylated Hydroxytoluene. Heat to about 85° C. and mix until uniform.
9. Add the mixture of Step 8 to the mixture of Step 7 with agitation. Mix until uniform.
10. While mixing, cool batch to about 37° C.
11. Add while mixing add the mixture of Step 4 and then add the mixture of Step 5. Mix until uniform.
12. Add while mixing Phenoxyethanol and Methylisothiazolinone.
13. While mixing add the mixture of Step 2, then the mixture from Step 3. Mix until uniform.
14. Add the *Belis Perennis* flower extract and mix until uniform.
15. While mixing add the mixture from Step 1 and mix until uniform.
16. Add the Hydroxyethyl acrylate, sodium acryloyldimethyltaurate copolymer, squalene and polysorbate 60. Mix until uniform.
17. While mixing add the mixture from Step 6. Mix until uniform.
18. While mixing add the Perfume. Mix until uniform.
19. This formulation has a pH ranging from 4.5-6.5; a viscosity ranging from 5,000 to 15,000 cP; and a density ranging from 1.01 to 1.06.

Alternative topical cosmetic composition comprising:

| Function | Component | % W/W |
| --- | --- | --- |
| 01. 1$^{st}$ Portion Purified Water | Vehicle | 46.470 |
| 02. 2$^{nd}$ Portion Purified Water | Vehicle | 5.000 |
| 03. 3$^{rd}$ Portion Purified Water | Vehicle | 5.000 |
| 04. 4$^{th}$ Portion Purified Water | Vehicle | 5.000 |
| 05. 5$^{th}$ Portion Purified Water | Vehicle | 2.000 |
| 06. Cetyl Alcohol | Thickener | 2.000 |
| 07. Butylhydroxytoluene | Antioxidant | 0.050 |
| 08. Disodium EDTA | Chelating Agent | 0.200 |
| 09. Sodium Metabisulfite | Antioxidant | 0.300 |
| 10. Ethylhexyl methoxycinnamate | Solar Filter | 7.500 |
| 11. Propylene Glycol | Solubilizer | 2.000 |
| 12. Triethanolamine 99W | Regulation of pH | 0.550 |
| 13. Methylene Bis-Benzotriazolyl Tetramethylbutylphenol (and) Decyl Glucoside (and) Xanthan Gum (and) Propylene glycol (and) Water (Ciba) | Solar Filter | 5.000 |
| 14. Cyclopentasiloxane/PEG/PPG-18/18 Dimethicone (Dow Corning) | Emollient | 2.000 |
| 15. Dimethicone Crosspolymer (and) Cyclomethicone (Dow Corning) | Emollient | 2.000 |
| 16. Hydroxyethyl Acrylate (and) Sodium Acryloyldimethyl Taurate Copolymer (and) Squalane (and) Polysorbate 60 (Chemyunion) | Thickener | 5.000 |
| 17. Phenoxyethanol (and) Methylisothiazolinone (Rohm & Haas) | Preservative | 0.570 |
| 18. C14/C22 Alcohol (and) C12/C20 Alkyl glucoside (Chemyunion) | Emulsifier | 2.000 |
| 19. Extract of Licorice (Bioland Ltd.) | Active | 0.060 |
| 20. Extract of *Bellis Perennis* (Chemisches Laboratorium Dr. Kurt Richter GmBh) | Active | 5.000 |
| 21. *Emblica* (Merck KGaA) | Active | 2.000 |
| 22. Fragrance FAV 22000 (FAV105) | Perfume | 0.300 |
| | | 100% |

Alternative Method of Manufacture of Alternative Composition

This alternative method achieved a change in formulation pH from a pH ranging from 4.0 to 6.5 to a pH ranging from 5.0 to 6.5. Extract of licorice, extract of *bellis perennis* and *emblica* were generally kept under yellow light and/or protected from exposure to white light. In one embodiment, the entire process, including packaging, preferably takes place under yellow light. In another embodiment, the resulting formulation is stored without exposure to white light and air.

Premixes

1. Premix A: In an additional suitable container add Tinosorb M® (Methylene Bis-Benzotriazolyl Tetramethylbutylphenol (and) Decyl Glucoside (and) Xanthan Gum (and) Propylene glycol (and) Water and Purified Water 2$^{nd}$ Portion. Agitate until totally dispersed. Reserve.
2. Premix B: In an additional suitable container add DC9040® (Dimethicone Crosspolymer (and) Cyclomethicone and DC5225C® (Cyclopentasiloxane/PEG/PPG-18/18 Dimethicone). Agitate until totally dispersed. Reserve.
3. Premix C: In an additional suitable container add Propylene Glycol and Licorice Extract. Agitate until totally dissolved. Reserve.
4. Premix D: In an additional suitable container add Emblica and Purified Water 3$^{rd}$ Portion Agitate until totally dispersed. Reserve.
5. Premix E: In an additional suitable container add Triethanolamine 99W and Purified Water 4$^{th}$ Portion. Agitate until totally diluted. Reserve.
6. Premix F: In an additional suitable container add Sodium Metabisulfite and Purified Water 5$^{th}$ Portion. Agitate until totally dissolved. Reserve.

Preparation of Oily Phase

7. In a suitable container, prepare the Oily Phase adding Cetyl Alcohol, Montanov L®(C14/C22 Alcohol C12/C20 Alkyl Glycoside), Ethylhexyl methoxycinnamate and Butylhydroxytoluene. Heat during agitation to 75° C.±2° C.

Preparation of Aqueous Phase

8. Add Purified Water 1$^{st}$ Portion and Disodium EDTA to the principal reactor. Heat to 75° C.±2° C. during agitation and homogenization.

Emulsion

9. When both phases reach 75°±2° C., pour oily phase over the aqueous phase, during intense agitation and homogenization. Check to see if the emulsion formed is homogenous after 15 minutes of homogenization. If necessary, agitate and homogenize for longer time.
10. Cool to 37° C.±2° C.
11. Add Premix D and agitate until completely homogenized.
12. Add Premix E, agitate and homogenize well for at least 15 minutes.
13. Add Premix A under intense agitation.
14. Add Neolone PE® (Phenoxyethanol (and) Methylisothiazolinone), Premix B, Premix C, and Belides® (Extract of Bellis Perennis). Agitate and homogenize until smooth.
15. Add Simugel NS® (Hydroxyethyl Acrylate (and) Acryloyldimethyl Copolymer (and) Sodium Taurate (and) Squalane (and) Polysorbate 60) to the main reactor under intense homogenization and incorporate agitation when all the material is in the tank. Agitate and homogenize well for at least 15 minutes.

16. Add Fragrance FAV 22000® and homogenize.
17. Add Premix F, agitate and homogenize well for at least 15 minutes.
18. Collect a sample from the top and from the bottom, measure the pH (range between 5.0 to 6.5). No variation in the results of the pH between the samples should be greater than 0.3 arbitrary pH units, which shows homogeneity. If necessary, continue agitating until the aforementioned parameter is attained.

Screening of Volunteers

1. POPULATION SAMPLING:

Ten (10) volunteers, of both sexes, of ages between 18 and 60 years old, were screened for the performance of the study. The subjects participating had the first four letters of the name and the first letter of the family name, an individual identification number (generated by electronic system) and a protocol number.

2. INCLUSION CRITERIA:

Age level: 18 to 60 years old;
Phototypes II and III, according to Fitzpatrick's classification;
Whole skin at test site;
Agreement to follow the assay procedures and to come to the clinic at the days and times determined for the evaluations;
Signature of the informed consent form.

3. EXCLUSION CRITERIA

Pregnancy or breastfeeding;
Use of anti-inflammatory or immunosuppressant drugs;
Personal precedents of atopy;
Use of topical or systemic photosensitizing medication;
History of phototoxic or photoallergic reactions;
History of sensitization or irritation to topic production;
Photo-induced pathologies, such as sun hives, lupus erythematosus, polyform rash at light, recurring herpes simplex;
Presence of active inflammatory dermatoses at test site;
Presence of nevus lesions at the test site;
Active skin pathologies;
History of sensitization or irritation to topic production;
Frequent exposure to sun or tanning beds;
In use of new innovative drugs within the last 6 months;

Methodology

1. METHODOLOGICAL PROCEDURES:

After the initial procedures, the minimum erythematose dose necessary to induce pigmentation in each volunteer, was determined as described below.

a. Calculation of the Minimum Erythematose Dose:

Each volunteer was subjected to a pre-test to evaluate the minimum erythematose dose (MED). A series of six exposures were applied to the unprotected skin of each volunteer, each one of them being 12% higher than the previous one, in geometric progression. The median dose was previously determined according to Fitzpatrick Phototype, shown in Table I below:

TABLE I

| Type | Color | Sensitivity | Reaction | MED |
| --- | --- | --- | --- | --- |
| I | White - Pale Light eyes and hair | Very Sensitive | Always burns, never tans | 0.85 |
| II | White | Very Sensitive | Always burns, never tans | 1 |
| III | Darker white | Sensitive | Burns moderately, tans moderately | 1.3 |
| IV | Light brown | Little Sensitive | Burns minimally, always tans | 1.75 |
| V | Brown | Little Sensitive | Burns rarely, always tans | 2.3 |
| VI | Black | Non-Sensitive | Never burns, always pigments | 4.6 |

After irradiation, the volunteers were dismissed and instructed to return after 24 hours. Exposure data was recorded for each volunteer.

b. Reading:

After irradiation, each volunteer was released and instructed to return within 24 hours, whereby the exposure site was read with the volunteer in a vertical position at a predetermined distance and illumination which was kept constant for each volunteer. The MED was then determined for each volunteer.

The individual Minimum Erythematose Dose (iMED) is defined as the minimum ultraviolet (UV) radiation dose necessary to produce clear and well-defined contour erythema at the exposure site, which was used as a reference during the test stage.

Accordingly, sub-sites not presenting erythema were a required criterion for the test evaluation. If this does not occur, new applications must be performed to determine the iMED.

c. Induction of Pigmentation:

After iMED determination, each test site, located on the back, between the pelvic and scapular waist, laterally to the medial line of the spine, was marked with the volunteer in a horizontal position and using a marker. Three sites indicated for the application of the products were delimited, i.e., Site B, Site E, and Site F. Each site was 35 cm$^2$ (07×05 cm). At each of the delimited sites, irradiation equivalent to 1.5 times the minimum erythematose dose, previously calculated for each volunteer, was applied. This application was repeated twice whereby each site was irradiated a total of three times.

d. Product Application:

After the irradiation, the volunteers were dismissed and instructed to return after 72 hours for photographic documentation and colorimetric evaluation of the sites. Subjects were tested in triplicate with each of Site B, E, and F corresponding to three distinct irradiation areas to provide a total of three test Sites and nine designation areas per subject. After evaluation, 2 mg of each test material was applied to a designated irradiation area of a test Site on each subject once daily according to the sequence below:

Site B: Hydroquinone 2%;
Site E: The present topical cosmetic composition;
Site F: Negative Control: Site with no product application.

In order to optimize the products permeation and avoid product migration, handling or UV exposure, the product application sites were occluded with filter paper, supported by a semi-permeable adhesive tape. The volunteer returned to the clinic for application, readings and evaluations according to Table II below.

TABLE II

|  | Fri T-3 | Mon T0 | Wed T02 | Fri T04 | Mon T07 | Wed T09 | Fri T11 | Mon T14 | Wed T16 | Fri T18 | Mon T21 |
|---|---|---|---|---|---|---|---|---|---|---|---|
| Dermatological Evaluation | X | | | | | | | | | | X |
| Colorimetric evaluation | | X | | | X | | | X | | | X |
| Photographic documentation | | X | | | X | | | X | | | X |
| Reading of irradiated site | X | X | | | | | | | | | |
| Products application | | X | X | X | X | X | X | X | X | X | X |
| UVB irradiation | X | | | | | | | | | | | e. Colorimetric Evaluation:

The colorimetric evaluation was performed using a CHROMA METER. All measurements were performed three times, the L*a*b* parameters average were recorded for each volunteer. The L* parameter was separately statistically analyzed, as its value decreases.

f. Statistics:

To check if there is a statistically significant difference between the treated and control sites and between the experimental timepoints, the parameter L* was compared. This comparison was made through t-student tests for paired data.

Results

The treatments were evaluated clinically and colorimetrically on day T7, T14 and T21. Site B which contained the positive control (Hydroquinone 2%) had the colorimetric average for each experimental time as shown in FIG. 1. FIG. 1 illustrates progressive lightening over time that becomes statistically significant after 21 days. Table III below shows the results of the comparison test between the L* of T0 averages and the other experimental times for area 1 (Site B). Table IV shows the raw data for the individual results for the area 1 (Site B) for each volunteer in term of L*, a*, and b* for each of T0, T07, T14, and T21.

TABLE III

| EVALUATED DIFFERENCE | P-VALUE | CONCLUSION * |
|---|---|---|
| T0 and T7 | 0.3626 | Does not reject the hypothesis. ** |
| T0 and T14 | 0.1049 | Does not reject the hypothesis. |
| T0 and T21 | 0.0182 | Rejects the hypothesis. |

* Level of Significance: 5%
** Hypothesis: there are no differences between the treated area and control area.

TABLE IV

Individual results of the hydroquinone treatment area

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 59.9 | 7.53 | 15.73 | 60.01 | 7.42 | 15.69 | 62.03 | 5.93 | 15.68 | 63.76 | 4.85 | 14.48 |
| 2 | 56.0 | 14.38 | 10.40 | 58.96 | 8.98 | 11.06 | 60.53 | 8.28 | 12.11 | 58.87 | 9.17 | 13.64 |
| 3 | 60.1 | 6.66 | 16.34 | 61.44 | 6.39 | 15.55 | 61.74 | 4.86 | 15.25 | 61.89 | 4.71 | 17.09 |
| 4 | 65.74 | 7.13 | 15.32 | 65.15 | 7.63 | 14.16 | 64.97 | 7.93 | 14.44 | 65.32 | 6.47 | 15.01 |
| 5 | 54.45 | 12.42 | 17.88 | 53.77 | 9.90 | 19.02 | 53.77 | 9.90 | 19.02 | 54.39 | 10.55 | 18.22 |
| 6 | 61.36 | 8.21 | 12.76 | 61.74 | 7.53 | 13.82 | 62.44 | 7.00 | 14.40 | 62.79 | 8.74 | 13.08 |
| 7 | 59.06 | 10.74 | 16.83 | 60.01 | 8.24 | 16.84 | 59.68 | 8.19 | 19.00 | 61.74 | 8.18 | 16.55 |
| 8 | 59.16 | 11.14 | 15.70 | 60.07 | 9.80 | 16.17 | 60.95 | 8.91 | 15.96 | 60.96 | 11.34 | 16.72 |
| 9 | 57.67 | 10.24 | 13.93 | 59.62 | 6.99 | 16.36 | 58.58 | 6.76 | 17.54 | 61.44 | 6.63 | 16.14 |
| 10 | 59.92 | 12.78 | 13.45 | 61.26 | 9.01 | 15.86 | 62.00 | 8.00 | 15.53 | 62.91 | 9.74 | 15.37 |

Figure 2:
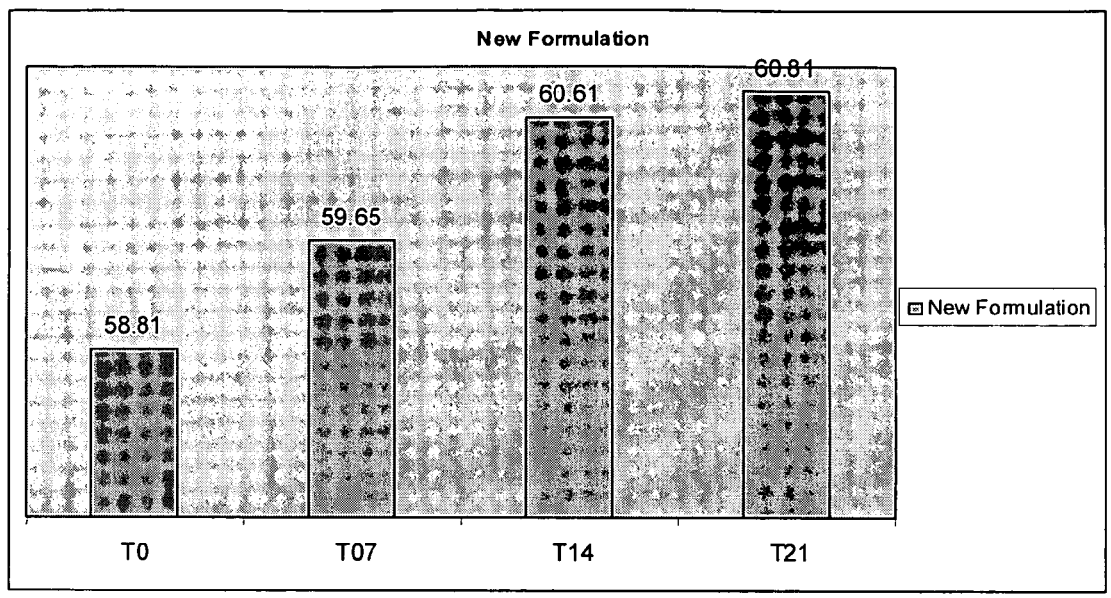
FIG. 2 illustrates progressive lightening over time that becomes statistically significant after 14 days for Site E treated with the present topical cosmetic composition.

FIG. 2 illustrates the results obtained for Site E, i.e., the application location of the evaluated present topical cosmetic composition. FIG. 2 illustrates that there is progressive lightening over time that becomes statistically significant after 14 days. Table V below illustrates the results of the comparison test between the L* of T0 averages and the other experimental times for area 2 (Site E). Table VI shows the raw data for the individual results for area 2 (Site E) for each volunteer in term of L*, a*, and b* for each of T0, T07, T14, and T21.

TABLE V

| EVALUATED DIFFERENCE | P-VALUE | CONCLUSION * |
|---|---|---|
| T0 and T07 | 0.2228 | Does not reject the hypothesis. ** |
| T0 and T14 | 0.0022 | Rejects the hypothesis. |
| T0 and T21 | 0.0020 | Rejects the hypothesis. |

* Level of Significance: 5%
** Hypothesis: there are no differences between the treated area and control area.

TABLE VII

| EVALUATED DIFFERENCE | P-VALUE | CONCLUSION * |
|---|---|---|
| T0 and T07 | 0.2220 | Does not reject the hypothesis. ** |
| T0 and T14 | 0.2386 | Does not reject the hypothesis. |
| T0 and T21 | 0.2039 | Does not reject the hypothesis. |

* Level of Significance: 5%
** Hypothesis: there are no differences between the treated area and control area.

TABLE VI

Individual results of the present topical cosmetic composition

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 58.82 | 10.34 | 14.33 | 61.55 | 6.50 | 14.68 | 62.66 | 7.49 | 13.97 | 64.68 | 4.01 | 15.29 |
| 2 | 55.96 | 15.97 | 11.69 | 57.50 | 8.82 | 10.81 | 59.20 | 9.68 | 12.34 | 60.17 | 8.06 | 12.51 |
| 3 | 61.33 | 7.02 | 16.55 | 61.99 | 6.41 | 15.87 | 61.23 | 5.78 | 15.16 | 62.97 | 6.00 | 16.77 |
| 4 | 63.82 | 8.53 | 14.95 | 62.64 | 9.37 | 14.60 | 62.69 | 9.03 | 15.85 | 62.01 | 9.48 | 15.40 |
| 5 | 54.76 | 10.98 | 18.08 | 55.08 | 9.53 | 18.29 | 55.08 | 9.53 | 18.29 | 55.22 | 9.90 | 18.66 |
| 6 | 60.89 | 7.76 | 14.01 | 60.64 | 8.61 | 14.83 | 61.81 | 6.78 | 15.30 | 62.32 | 8.39 | 13.50 |
| 7 | 60.34 | 9.17 | 16.28 | 60.69 | 7.98 | 16.54 | 60.27 | 7.03 | 18.05 | 60.67 | 9.09 | 17.34 |
| 8 | 58.65 | 11.75 | 15.60 | 58.64 | 11.23 | 15.51 | 60.90 | 8.60 | 16.34 | 62.28 | 10.52 | 14.14 |
| 9 | 57.75 | 10.59 | 15.10 | 59.00 | 7.54 | 16.11 | 61.44 | 5.36 | 16.50 | 63.43 | 6.39 | 14.44 |
| 10 | 59.72 | 10.61 | 15.83 | 60.66 | 8.59 | 15.77 | 61.41 | 7.27 | 13.70 | 62.17 | 9.39 | 16.58 |

Figure 3:
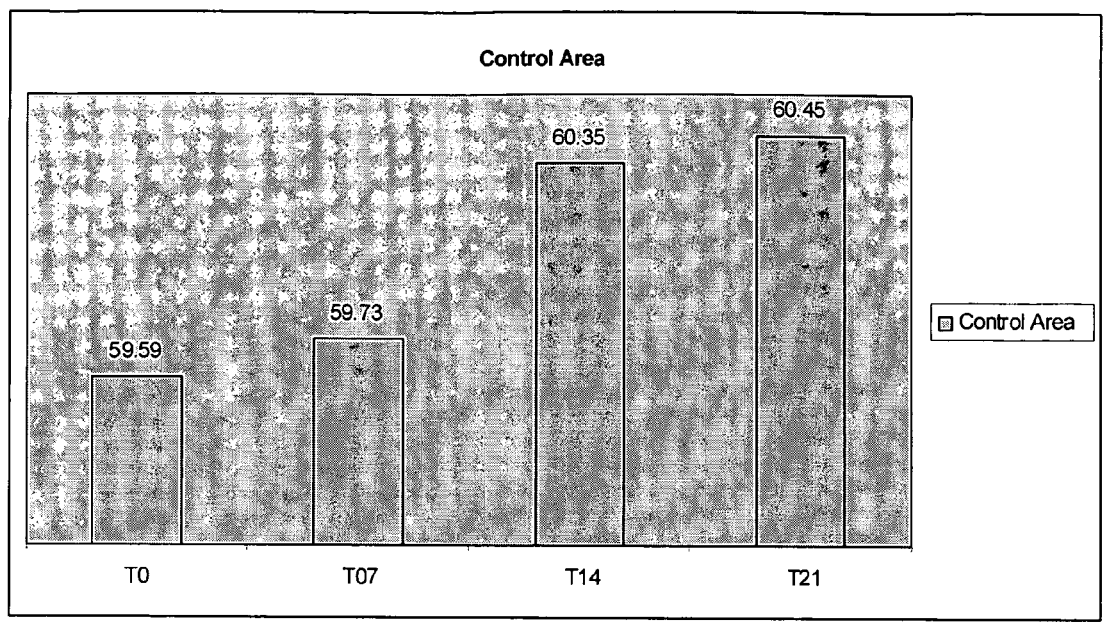
FIG. 3 illustrates progressive lightening (natural degradation of the synthesized melanin), without any significance over the experimental times for the control location (Site F) which was not treated.

FIG. 3 illustrates, for the control location Site F, i.e., where there was no treatment for the irradiation, progressive lightening (natural degradation of the synthesized melanin), without any significance over the experimental times. Table VII below shows the results of the comparison test between the L* of T0 averages and the other experimental times for the control area (Site F). Table VIII shows the raw data for the individual results for the control area (Site F) for each volunteer in term of L*, a*, and b* for each of T0, T07, T14, and T21.

TABLE VIII

Individual results of the control area

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 59.14 | 9.94 | 18.73 | 58.38 | 6.89 | 17.12 | 60.71 | 5.48 | 15.25 | 61.01 | 4.32 | 16.09 |
| 2 | 57.38 | 13.43 | 11.23 | 57.72 | 9.40 | 12.29 | 58.80 | 8.28 | 13.08 | 57.63 | 6.68 | 14.60 |
| 3 | 60.69 | 7.01 | 17.36 | 60.76 | 5.08 | 16.74 | 59.05 | 4.85 | 16.93 | 60.54 | 3.89 | 16.60 |
| 4 | 67.55 | 5.62 | 16.95 | 65.16 | 6.98 | 15.57 | 64.54 | 6.83 | 16.21 | 64.12 | 6.52 | 16.70 |
| 5 | 53.18 | 11.24 | 18.46 | 54.10 | 8.04 | 19.13 | 54.10 | 8.04 | 19.13 | 54.22 | 8.53 | 19.96 |
| 6 | 62.73 | 8.22 | 13.81 | 62.86 | 6.29 | 13.85 | 62.34 | 5.87 | 15.20 | 63.19 | 7.10 | 13.15 |
| 7 | 57.51 | 10.47 | 18.63 | 59.11 | 7.91 | 17.33 | 59.67 | 5.92 | 19.21 | 60.97 | 7.70 | 18.03 |
| 8 | 58.68 | 11.31 | 15.10 | 59.69 | 9.20 | 17.29 | 61.96 | 7.41 | 16.20 | 59.31 | 12.23 | 17.90 |
| 9 | 59.68 | 8.49 | 15.60 | 59.91 | 7.05 | 17.01 | 62.05 | 5.53 | 15.59 | 63.37 | 7.12 | 11.30 |
| 10 | 59.33 | 12.14 | 14.27 | 59.60 | 7.99 | 16.56 | 60.29 | 7.13 | 16.40 | 60.15 | 9.00 | 17.06 |

Figure 4:
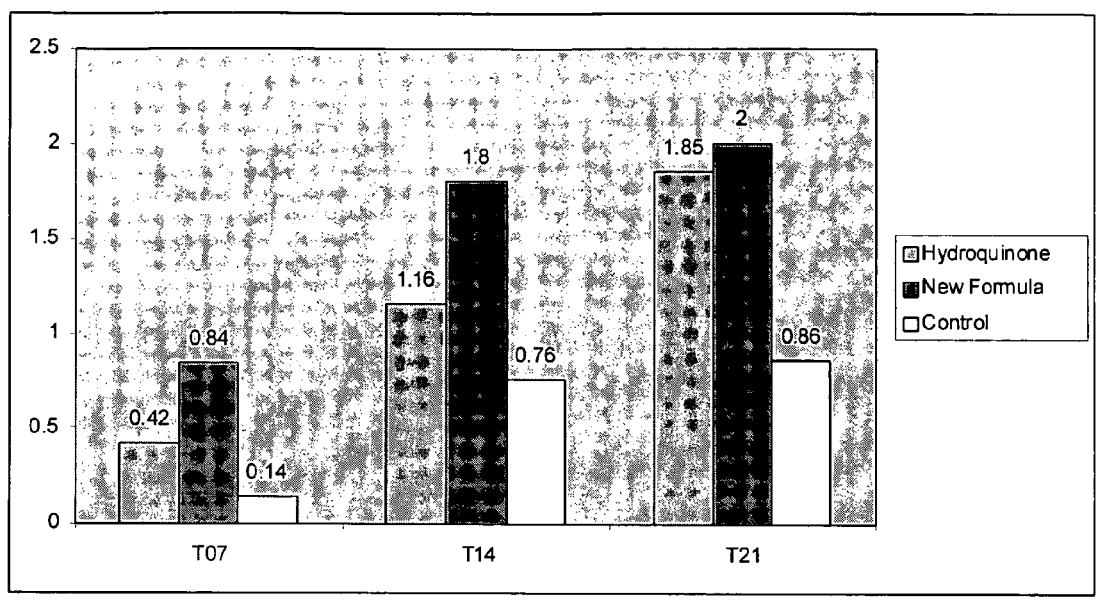
FIG. 4 illustrates the comparison between the averages of the colorimetric values in treatments 1 (Site B) and 2 (Site E) and the control (Site F) over the evaluation times.

FIG. 4 illustrates the comparison between the averages of the colorimetric values in treatments 1 and 2 and the control over the evaluation times. Table IX illustrates that only the present topical cosmetic formulation exhibited statistically significant reduction in pigmentation as compared to the spontaneous reduction in pigmentation observed in the control group.

TABLE IX

| EVALUATED DIFFERENCE | P-VALUE | CONCLUSION * |
|---|---|---|
| New formulation and Hydroquinone | 0.13 | Does not reject the hypothesis. ** |
| New formulation and Control | 0.02 | Rejects the hypothesis. |
| Hydroquinone and Control | 0.10 | Does not reject the hypothesis. **tks |

\* Level of Significance: 5%
\*\* Hypothesis: there are no differences between the areas.

Discussion

In an experimental model with UV radiation induced pigmentation (melanogenesis) and having no preexisting pigmentary dysfunction, clinical pigmentation will be reduced spontaneously over time, on the treated areas. All locations, including the untreated control, exhibited a significant reduction in pigmentation up to T21 as evaluated using a colorimeter.

Therefore, this experiment was carried out to comparatively evaluate which treatments would cause the quickest and most significant depigmentation. Because all of the treatments were applied simultaneously to each volunteer, the variable of melanization capacity was significantly reduced. Accordingly, depigmentation would occur at the same speed on all of the tested locations, in each volunteer.

Starting from this premise, the lightening effect was clinically observed over time for each location, which has already allowed for a visual evaluation and a comparative analysis.

To improve the accuracy of these observations and to allow for objective, consistent, and reproducible evaluation, the colorimeter was used as a complementary instrumental evaluation, enabling the detection of differences which the human eye cannot detect.

According to the colorimetry, the L* parameter provided by the colorimetric measurement is the index directly related to the skin's luminosity. The higher the value of L* the lighter the evaluated region.

Clinically and colorimetrically evaluating the treatments the progressive depigmentation was expected, as it deals with an experimental melanization phenomenon. The irradiated but untreated control locations, presented a significant colorimetric improvement of L* as from T21, with the hydroquinone; nevertheless, the lightening levels, when compared to the hydroquinone on T07 and T14, were statistically lower.

Still considering the data over time, the results differ in the following manner: Hydroquinone: significantly improves as from T21; The present topical cosmetic composition: significantly improves as from T14, with statistically significant higher lightening levels when compared to the control. Accordingly, the present topical cosmetic composition provided a faster and more significant lightening effect (provides a higher lightening index) as compared to hydroquinone.

Figure 5:
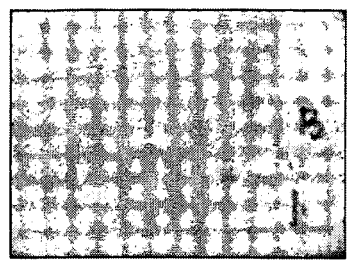
FIG. 5 illustrates photographs of clinical data supporting the colorimetric results in treatments 1 (Site B) and 2 (Site E) and the control (Site F) comparing evaluation times T0 and T21.
Figure 5:
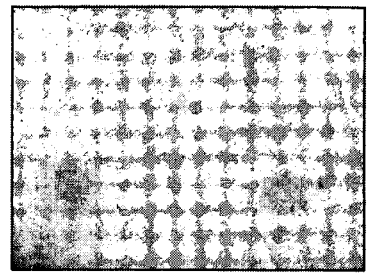
Figure 5:
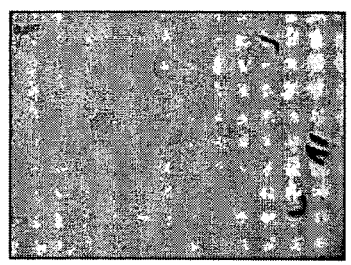
Figure 5:
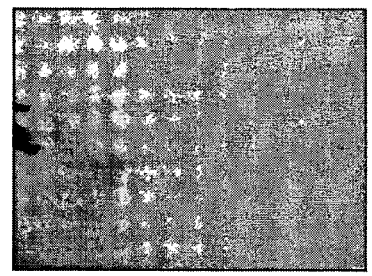
Figure 5:
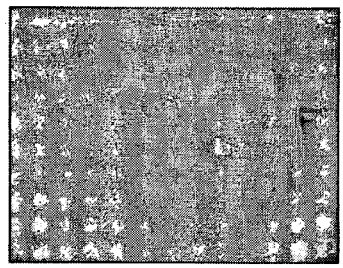
Figure 5:
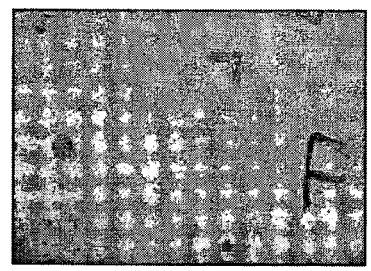

FIG. 5 shows photographs of clinical data supporting the colorimetric results, where the greater average lightening effect was obtained on the location with the new formula. The hydroquinone treatment and the new formulation were similar at the end of the study, although the new formulation is faster and provides a higher lightening index.

Example 2

The following example illustrates the preparation of a cream in accordance with the presently described subject matter:

| Component | Function | % W/W |
|---|---|---|
| Purified water | carrier | 62.250 |
| Cetyl alcohol | thickening agent | 2 |
| Xanthan gum | thickening agent | .2 |
| Butylated hydroxytoluene | antioxidant | .050 |
| C14-22 alcohols and C12-20 alkylglucoside | emulsifier | 2 |
| Potassium cetyl phosphate | emulsifier | 1 |
| Glyceryl stearate and PEG-100 stearate | emulsifier | 2 |
| Cyclomethicone | emollient | 2 |
| Disodium edetate | chelating agent | .2 |
| *Bellis perennis* flower extract | antioxidant/active | 5 |
| *Phyllanthus Embilica* Fruit Extract | antioxidant/active | 2 |
| Licorice extract | antioxidant/active | .050 |
| Phenoxyethanol and methylisothiazolinone | preservative | .6 |
| Perfume FAV22000-Essential Oils Blend | fragrance | .3 |
| Hydroxyethyl acrylate, Sodium acryloyldimethyltaurate copolymer, Squalane, and Polysorbate 60 | thickening agent | 5 |
| Sodium metabissulfite | antioxidant | .3 |
| Methylene bis-benzotriazolyl tetramethylphenol | sunscreen active | 5 |
| Ethylhexyl Methoxycinnamate | sunscreen active | 7.5 |
| Propylene Glycol | emollient | 2 |
| Triethanolamine | pH adjuster | .55 |
| | | 100.0% |

The composition is prepared as in Example 1. More specifically, after Premix E is added to the emulsion, Neolone PE (Phenoxiethanol and Methylisothiazolinone) and cyclomethicone are added under high shearing homogenization and mixing for about 15 minutes. The thickening agents including xanthan gum are added in the oil phase.

Example 3

The following example illustrates the preparation of a cream in accordance with the presently described subject matter:

| Component | Function | % W/W |
|---|---|---|
| Purified water | carrier | 63.43 |
| Butylated hydroxytoluene | antioxidant | 0.05 |
| Disodium edetate | chelating agent | 0.20 |
| Propylene glycol | emollient | 2.00 |
| *Phyllanthus embilica* fruit extract | antioxidant/active | 2.00 |
| Hydroxyethyl acrylate, Sodium acryloyldimethyltaurate copolymer, Squalane, and Polysorbate 60 | thickening agent | 5.00 |
| Methylene bis-benzotriazolyl tetramethylphenol | sunscreen active | 5.00 |
| *Bellis perennis* extract | antioxidant/active | 5.00 |
| Cyclopentasiloxane dimethicone crosspolymer | emollient | 2.00 |
| Cyclopentasiloxane PEG/PPG-18/18 dimethicone | emollient | 2.00 |
| Phenoxyethanol and methylisothiazolinone | preservative | 0.60 |
| Triethanolamine | pH adjuster | 0.57 |
| Perfume | perfume | 0.30 |
| Cetyl alcohol | thickening agent | 2.00 |
| C14-22 alcohols and C12-20 alkylglucoside | emulsifier | 2.00 |
| Ethylhexyl methoxycinnamate | sunscreen active | 7.50 |
| Sodium metabissulfite | antioxidant | 0.30 |
| Licorice extract | antioxidant/active | 0.05 |
| | | 100.0% |

The composition was prepared as in Example 1.

Example 4

The following example illustrates a generally applicable method for administering a composition in accordance with the presently described subject matter:

A topical cosmetic composition is administered topically to the skin of a subject being treated by conventional means. This is preferably done through the use of a serum or cream gel formulation. A topical preparation may thus be applied to the desired skin surface area with, for example, the use of the fingertips.

For topical administration of the cosmetic composition, the subject should be told to first clean the affected area gently and to pat it dry. The topical cosmetic composition may then be applied directly to the affected skin area or dispensed into the palm of the hand or suitable vessel from which material may be taken and manually applied to the skin area to be treated.

Example 5

A subject is suffering from undesired skin pigmentation. A topical cosmetic composition as described herein is topically administered to undesirably pigmented areas of the skin of the subject. It would be expected that the undesirably pigmented areas of the skin of the subject would be lightened.

Example 6

A subject is suffering from vitiligo. A topical cosmetic composition as described herein is topically administered to the residual areas of normal skin of the subject. It would be expected that the residual areas of normal skin of the subject would be lightened to impart a homogeneous color to the entire skin.

Example 7

A subject is suffering from age spots. A topical cosmetic composition as described herein is topically administered to the affected skin areas of the subject. It would be expected that the age spots would be lightened.

All publications cited in the specification are indicative of the level of skill of those skilled in the art to which the presently described subject matter pertains. All of these publications are hereby incorporated by reference herein to the same extent as if each individual publication were specifically and individually indicated as being incorporated by reference.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A topical cosmetic composition, consisting of:
   a) a skin lightening component consisting of:
      a *Phyllanthus* extract;
      a *Bellis* extract; and
      a licorice extract;
   b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA; and
   c) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a free radical scavenger, a preservative, an emulsifier, a humectant, a moisturizer, a suspending agent, a surfactant, an optical brightener, a stabilizer, a penetration enhancer, a perfume, a coloring agent, a fluid alkyl alcohol, a polysiloxane, a modified polysiloxane and combinations thereof.

2. The topical cosmetic composition of claim 1, wherein the *Phyllanthus* extract comprises a *Phyllanthus embilica* extract and the *Bellis* extract comprises a *Bellis perennis* extract.

3. The topical cosmetic composition of claim 2, wherein the *Phyllanthus embilica* extract comprises a *Phyllanthus embilica* fruit extract; the *Bellis perennis* extract comprises a *Bellis perennis* flower extract; and the licorice extract comprises a licorice root extract.

4. The topical cosmetic composition of claim 3, wherein the *Phyllanthus embilica* extract is present in an amount of from about 0.25 wt % to about 4 wt %; the *Bellis perennis* extract is present in an amount of from about 1 wt % to about 20 wt %; and the licorice extract is present in an amount of from about 0.01 wt % to about 2 wt %, based on the total weight of the composition.

5. The topical cosmetic composition of claim 1, wherein the at least one sunscreen contains a first sunscreen selected from the group consisting of methylene bis-benzotriazolyl tetramethylbutylphenol, diethylamino hydroxybenzoyl hexyl benzoate, coated zinc oxide, and combinations thereof.

6. The topical cosmetic composition of claim 1, wherein the at least one sunscreen containing the first sunscreen further contains a second sunscreen selected from the group consisting of ethylhexyl methoxycinnamate, isoamyl methoxycinnamate, homosalate, ethyl hexyl salicilate, octocrylene, polysilicone-15, butyl methoxydibenzoylmethane, menthyl anthranilate, ethylhexyl dimethyl PABA, and combinations thereof.

7. The topical cosmetic composition of claim 1, wherein the at least one sunscreen is methylene bis-benzotriazolyl tetramethylbutylphenol.

8. The topical cosmetic composition of claim 2, wherein the at least one cosmetically acceptable carrier is water.

9. The topical cosmetic composition of claim 8, wherein the water is present in an amount of from about 3 wt % to about 95 wt %, based on the total weight of the composition.

10. A method of lightening skin pigmentation in a subject, comprising topically administering to skin of a subject in need thereof, a therapeutically effective amount of the topical cosmetic composition of claim 1.

11. A topical cosmetic composition, consisting of:
    (a) a skin lightening component consisting of:
       a *Phyllanthus embilica* extract present in an amount of from about 0.25 wt % to about 4 wt %;
       a *Bellis perennis* extract present in an amount of from about 1 wt % to about 20 wt %; and
       a licorice extract present in an amount of from about 0.01 wt % to about 2 wt %;
    (b) water;
    (c) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of from about 0.5 wt % to 30 wt %; and
(d) at least one non-skin lightening agent selected from
i) an anti-acne agent,
ii) an anti-microbial agent,
iii) an anti-wrinkle agent,
iv) an anti-atrophy agent,
v) an anti-inflammatory agent,
vi) an optical brightener, and
vii) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a gelling agent, a free radical scavenger, a preservative, an emulsifier, a humectant, a moisturizer, a suspending agent, a surfactant, a stabilizer, a vitamin, a penetration enhancer, a perfume, a coloring agent, a fluid alkyl alcohol, a polysiloxane, a modified polysiloxane, and
viii) a combination of any of i) - vii) thereof.

12. The topical cosmetic composition of claim 6, wherein the first sunscreen is present in an amount of from about 1 wt % to 20 wt %, and the second sunscreen is present in an amount of from about 1 wt % to about 10 wt %, based on the total weight of the topical cosmetic composition.

13. The topical cosmetic composition of claim 6, wherein the second sunscreen is ethylhexyl methoxycinnamate.

14. The topical cosmetic composition of claim 6, wherein the first sunscreen is methylene bis-benzotriazolyl tetramethylbutylphenol, and the second sunscreen is ethylhexyl methoxycinnamate.

15. A topical cosmetic composition, consisting of:
a) a skin lightening component consisting of:
a *Phyllanthus* extract;
a *Bellis* extract; and
a licorice extract;
b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of from about 0.5 wt % to 30 wt %; and
c) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a preservative, an emulsifier, a humectant, a moisturizer, a suspending agent, an optical brightener, a stabilizer, a penetration enhancer, a perfume, a coloring agent, and combinations thereof; provided that the composition does not comprise at least one oligopeptide that is not normally present in the *Phyllanthus* extract, the *Bellis* extract, and the licorice extract.

16. A topical cosmetic composition, consisting of:
a) a skin lightening component consisting of:
a *Phyllanthus* extract;
a *Bellis* extract; and
a licorice extract;
b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of from about 0.5 wt % to 30 wt %; and
c) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a preservative, an emulsifier, a humectant, a moisturizer, a suspending agent, an optical brightener, a stabilizer, a penetration enhancer, a perfume, a coloring agent, and combinations thereof;
provided that the composition does not comprise i) at least one oligopeptide that is not normally present in the *Phyllanthus* extract, the *Bellis* extract, and the licorice extract; or ii) hydroquinone.

17. A topical cosmetic composition, consisting of:
a) a skin lightening component consisting of:
a *Phyllanthus* extract;
a *Bellis* extract; and
a licorice extract;
b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of from about 0.5 wt % to 30 wt %; and
c) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a preservative, an emulsifier, a humectant, a moisturizer, a suspending agent, an optical brightener, a stabilizer, a penetration enhancer, a perfume, a coloring agent, and combinations thereof;
provided that the composition does not comprise i) at least one oligopeptide that is not normally present in the *Phyllanthus* extract, the *Bellis* extract, and the licorice extract; or ii) hydroquinone; or iii) a polyorganosiloxane containing epsilon-polylysine compound.

18. A topical cosmetic composition, consisting of:
a) a skin lightening component consisting of:
a *Phyllanthus* extract;
a *Bellis* extract; and
a licorice extract;
b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of from about 0.5 wt % to 30 wt %; and c) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a preservative, an emulsifier, a humectant, a moisturizer, a suspending agent, an optical brightener, a stabilizer, a penetration enhancer, a perfume, a coloring agent, and combinations thereof;
 provided that the composition does not comprise i) at least one oligopeptide that is not normally present in the *Phyllanthus* extract, the *Bellis* extract, and the licorice extract; or
 ii) hydroquinone; or
 iii) a polyorganosiloxane containing epsilon-polylysine compound; or
 iv) a flavan.

19. The composition according to claim 15, wherein the sunscreen in the composition provides for an SPF of greater than about 10.

20. The composition according to claim 16, wherein the sunscreen in the composition provides for an SPF of greater than about 10.

21. The composition according to claim 17, wherein the sunscreen in the composition provides for an SPF of greater than about 10.

22. The composition according to claim 18, wherein the sunscreen in the composition provides for an SPF of greater than about 10.

23. The composition according to claim 1, wherein the sunscreen in the composition provides for an SPF of greater than about 10.

24. A topical cosmetic composition consisting of:
a) a skin lightening component consisting of:
 a *Phyllanthus* extract;
 a *Bellis* extract; and
 a licorice extract;
b) at least one sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA which is present in an amount of about 0.5 to about 30% ww and
has an SPF of greater than about 10;
c) at least one non-skin lightening agent selected from
 i) an anti-acne agent,
 ii) an anti-microbial agent,
 iii) an anti-wrinkle agent,
 iv) an anti-atrophy agent,
 v) an anti-inflammatory agent,
 vi) an optical brightener, and
 vii) at least one cosmetically acceptable carrier selected from the group consisting of distilled water, saline, Ringer's solution, dextrose solution, Hanks solution and DMSO, and at least one cosmetically acceptable excipient selected from the group consisting of an antioxidant, a chelating agent, a pH adjuster, an emollient, a thickening agent, a gelling agent, a free radical scavenger, a preservative, an emulsifier, a humectant, a moisturizer, a suspending agent, a surfactant, a stabilizer, a vitamin, a penetration enhancer, a perfume, a coloring agent, a fluid alkyl alcohol, a polysiloxane, a modified polysiloxane, and
 viii) a combination of any of i) - vii) thereof.

\* \* \* \* \*